US00PP12055P2

(12) United States Plant Patent
Zary

(10) Patent No.: US PP12,055 P2
(45) Date of Patent: Aug. 14, 2001

(54) SHRUB ROSE PLANT NAMED 'JACRULAV'

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 09/405,426

(22) Filed: Sep. 22, 1999

(51) Int. Cl.[7] ..... A01H 5/00
(52) U.S. Cl. ..... Plt./108
(58) Field of Search ..... Plt./102, 107, 108

*Primary Examiner*—Howard J. Locker
(74) *Attorney, Agent, or Firm*—Klarquist Sparkman Campbell Leigh & Whinston, LLP

(57) ABSTRACT

A shrub rose plant having repeat flowering of five petaled, dark pink flowers of strong fragrance; an upright, well-branched habit of growth; and excellent disease resistance.

1 Drawing Sheet

1

The present invention relates to a new and distinct variety of rose plant of the shrub class which was originated by me by crossing the variety Pirette (not patented), with the variety Pirette (not patented).

The primary objective of this breeding was to examine the variability within the hybrid rugosa variety 'Pirette'. Ripe, self-pollinated hips were collected and seed harvested. The 618 seeds collected were germinated and several seedlings were selected and propagated by softwood cuttings. 'JACrulav' was eventually selected as a single plant as being significantly different and superior to its parent Pirette, differing from the latter in having only five petals of Red Group 53C versus Pirette's fifteen to twenty petals of Red-Purple Group 61C. Those and the following combination of characteristics are outstanding in the new variety and distinguish it from its parent, as well as from all other varieties of which I am aware:

1. Dark pink blooms;
2. Repeat flowering;
3. Upright, well-branched habit of growth;
4. Excellent disease resistance; and
5. Strong fragrance.

Asexual reproduction of this new variety by softwood cuttings, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Pirette (not patented).

*Pollen parent.*—Pirette (not patented).

Classification:

*Botanical.*—Hybrid *Rosa rugosa.*

*Commercial.*—Shrub.

2

FLOWER

Observations made from specimens grown in a garden environment at Somis, Calif. from March 1997 to December 1998.

Blooming habit: Continuous.

Bud:

*Size.*—1¼ inches long when the petals start to unfurl.

*Form.*—The bud form is long; pointed ovoid.

*Color.*—When sepals first divide, bud color is Red Group 46C. When half blown, the upper and lower sides of the petals are Red Group 53C.

*Sepals.*—Color: Green Group 138B. Surface texture: Covered in fine hairs. There are five unappendaged sepals.

*Receptacle.*—Color: Green Group 138B. Shape: Apple. Size: Medium (about 7/16 inch×3/8 inch.) Surface: Smooth.

*Peduncle.*—Length: Short (about 1 inch). Surface: Hairy. Color: Yellow-Green Group 147D. Strength: Stiff; erect.

Bloom:

*Size.*—Medium. Average open size is 3½ inches.

*Borne.*—Singly and several together in flat clusters of three to seven blooms.

*Stems*—Strength: Strong. Average length is about 14 to 18 inches.

*Form.*—When first open: Cupped. Permanence: Retains its form to the end.

*Petalage.*—Number of petals under normal conditions: 5.

*Color.*—The upper sides of the petals are Red Group 53C. The reverse sides of the petals are Red Group 53C. The base of each petal has on the upper and lower surface a distinct, White Group 155B petal spot that extends up the petal for about ¼ inch. The major color on the upper side is Red Group 53C.

*Variegations.*—None.

*Discoloration.*—The general tonality at the end of the first day: No change. At the end of the third day: A general fading in the open flower to Red Group 53D.

*Fragrance.*—Strong; cloves.

Petals:

*Texture.*—Thin.

*Shape.*—Oval.

*Form.*—Cupped.

*Arrangement.*—Imbricated. There are no petaloids in the center.

*Persistence.*—Petals drop off cleanly before drying.

*Lastingness.*—On the plant: Short (about four to five days). As a cut flower: Short (about five to six days).

Reproductive parts:

*Anthers.*—Size: Medium. Quantity: Many. Color: Yellow Group 13D. Arrangement: Regular around styles.

*Filaments.*—Color: Red Group 50D.

*Pollen.*—Present.

*Styles*—Color: Yellow-Green Group 154D. Very short.

*Stigmas.*—Color: Yellow-Green Group 154D.

Plant:

*Form.*—Shrub.

*Growth.*—Vigorous; upright; branching. At maturity, height is 3½ to 4 feet, width is 3 to 3½ feet.

Foliage: Number of leaflets on normal mid-stem leaves: Seven, nine or eleven.

*Size*—Large (7 inches long×4½ inches wide).

*Quantity.*—Abundant.

*Color.*—New foliage: Upper and lower surfaces: Yellow-Green Group 146C. Old foliage: Upper surface: Green Group 136A. Lower surface: Green Group 136C.

Leaflets:

*Shape*—Oval.

*Texture.*—Glossy; rugose.

*Edge.*—Serrated.

*Serration.*—Single; small.

*Petiole rachis.*—Color: Yellow-Green Group 147C.

*Petiole underside.*—Smooth; with prickles.

*Stipules.*—Long (about ¾ inch), serrated; bearded.

*Disease resistance.*—Resistant to mildew, blackspot and rust under normal growing conditions.

Wood:

*New wood.*—Color: Yellow-Green Group 147D. Bark: Smooth.

*Old wood.*—Color: Yellow-Green Group 147C. Bark: Smooth.

Prickles:

*Quantity.*—On main canes from base: Many. On laterals from main canes: Many.

*Form.*—Long; medium; short; straight and upward.

*Color when young.*—Yellow-Green Group 147D.

*Color when mature.*—Greyed-Orange Group 166B.

Small prickles:

*Quantity.*—On main stalks: Many. On laterals: Many.

*Color.*—When young: Yellow-Green Group 147D. When mature: Greyed-Orange Group 166B.

I claim:

1. A new and distinct variety of rose plant of the shrub class, substantially as herein shown and described, characterized particularly by its repeat flowering of five petaled, dark pink flowers of strong fragrance; an upright, well-branched habit of growth; and excellent disease resistance.

* * * * *

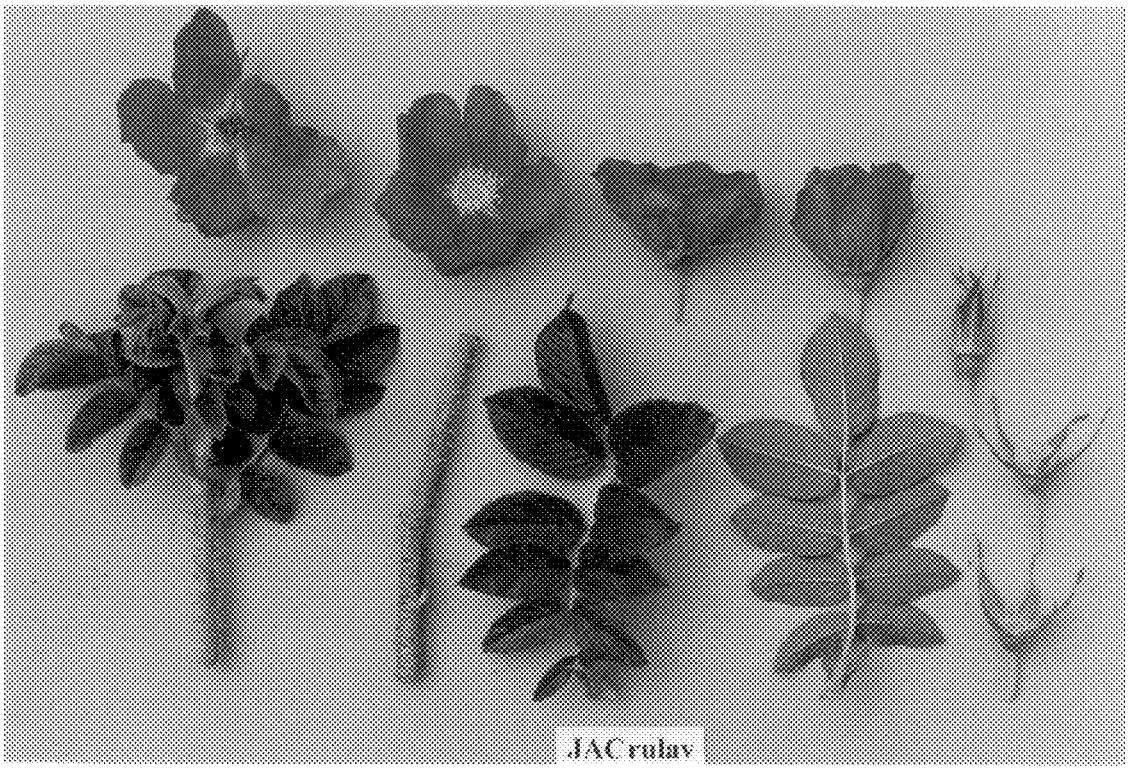
JAC rulav